United States Patent
Mugnier

(10) Patent No.: US 9,796,074 B2
(45) Date of Patent: Oct. 24, 2017

(54) REMOVABLE HANDLE PROVIDED WITH A DEVICE FOR DETACHABLE ASSEMBLY

(71) Applicant: ETABLISSEMENTS MAURICE MARLE, Nogent (FR)

(72) Inventor: Lionel Mugnier, Vitry les Nogent (FR)

(73) Assignee: ETABLISSEMENTS MAURICE MARLE, Nogent (FR)

( * ) Notice: Subject to any disclaimer, the term of this patent is extended or adjusted under 35 U.S.C. 154(b) by 26 days.

(21) Appl. No.: 14/783,101

(22) PCT Filed: Apr. 10, 2014

(86) PCT No.: PCT/FR2014/050878
§ 371 (c)(1),
(2) Date: Oct. 8, 2015

(87) PCT Pub. No.: WO2014/167258
PCT Pub. Date: Oct. 16, 2014

(65) Prior Publication Data
US 2016/0059403 A1 Mar. 3, 2016

(30) Foreign Application Priority Data
Apr. 11, 2013 (FR) ...................... 13 53260

(51) Int. Cl.
*A61B 17/17* (2006.01)
*B25G 3/04* (2006.01)
(Continued)

(52) U.S. Cl.
CPC ............... *B25G 3/04* (2013.01); *A61B 17/14* (2013.01); *A61B 17/1659* (2013.01);
(Continued)

(58) Field of Classification Search
CPC ............ F16B 13/0816; F16B 13/0858; A61B 2017/00464; A61B 17/1664;
(Continued)

(56) References Cited

U.S. PATENT DOCUMENTS 2,968,205 A * 1/1961 Springate .............. B25B 31/005
29/441.1
3,208,318 A * 9/1965 Roberts ............... B25B 23/0035
403/325
(Continued)

FOREIGN PATENT DOCUMENTS

EP 1 832 248 9/2007
FR 2 924 771 6/2009

OTHER PUBLICATIONS

International Search Report dated Jul. 17, 2014 in International (PCT) Application No. PCT/FR2014/050878.

*Primary Examiner* — David Bates
(74) *Attorney, Agent, or Firm* — Wenderoth, Lind & Ponack, L.L.P.

(57) ABSTRACT

The present invention relates to a removable handle (1) for a surgical rasp (2) or similar, the handle (1) and the rasp (2) cooperating, at right angles to their joining ends, via contact faces which at least intersect the mean direction of transmission of the forces between the handle (1) and the rasp (2), said handle (1) having a detachable assembly device (5) and being characterized in that the detachable assembly device (5) has, on the one hand, a means of assembly (6) by engagement in a direction generally perpendicular to said contact faces and using at least two complementary elements, namely a hollow tenon (7) and a mortice (8), and, on the other hand, a locking means (9) for locking said complementary elements (7, 8) in their engaged position, that is to say when the removable handle (1) and the rasp (2) are
(Continued)

joined together, with their contact faces applied against each other.

20 Claims, 2 Drawing Sheets

(51) Int. Cl.
*A61F 2/46* (2006.01)
*A61B 17/16* (2006.01)
*A61B 17/14* (2006.01)
*B25G 3/28* (2006.01)
*A61B 17/00* (2006.01)
*A61F 2/30* (2006.01)

(52) U.S. Cl.
CPC ........ *A61B 17/1668* (2013.01); *A61F 2/4607* (2013.01); *B25G 3/28* (2013.01); *A61B 2017/00464* (2013.01); *A61B 2017/00477* (2013.01); *A61F 2002/30479* (2013.01)

(58) Field of Classification Search
CPC . A61B 17/1659; A61B 17/175; A61B 17/922; A61B 17/1735; B25G 3/28; A61F 2002/4624
See application file for complete search history.

(56) References Cited

U.S. PATENT DOCUMENTS

| | | | | |
|---|---|---|---|---|
| 4,587,964 A * | 5/1986 | Walker | ............... | A61B 17/1659 606/85 |
| 5,089,003 A * | 2/1992 | Fallin | ................ | A61B 17/1659 606/53 |
| 5,190,550 A * | 3/1993 | Miller | ................ | A61B 17/1659 606/85 |
| 5,324,293 A * | 6/1994 | Rehmann | ........... | A61B 17/1659 606/85 |
| 5,443,471 A * | 8/1995 | Swajger | ............. | A61B 17/1659 403/294 |
| 5,531,750 A * | 7/1996 | Even-Esh | .......... | A61B 17/1659 606/79 |
| 5,702,391 A * | 12/1997 | Lin | .......................... | A61F 2/446 606/60 |
| 5,702,481 A * | 12/1997 | Lin | ....................... | A61F 2/3662 424/423 |
| 5,713,906 A * | 2/1998 | Grothues-Spork | | A61B 17/1604 606/86 R |
| 5,720,750 A * | 2/1998 | Koller | ................ | A61B 17/1659 606/85 |
| 5,800,547 A * | 9/1998 | Schafer | .................... | A61F 2/442 623/17.16 |
| 6,205,884 B1 * | 3/2001 | Foley | ................. | A61B 17/1659 606/85 |
| 6,626,913 B1 * | 9/2003 | McKinnon | .............. | A61F 2/367 606/86 R |
| 6,663,636 B1 * | 12/2003 | Lin | ..................... | A61B 17/1659 606/79 |
| 7,621,921 B2 * | 11/2009 | Parker | ....................... | A61F 2/34 606/91 |
| 7,976,548 B2 * | 7/2011 | Burgi | .................... | A61B 17/162 606/99 |
| 8,277,457 B1 * | 10/2012 | Burgi | .................... | A61F 2/4609 606/81 |
| 8,337,504 B2 * | 12/2012 | Surma | .................... | A61F 2/4607 606/86 R |
| 8,449,548 B2 * | 5/2013 | Nelson | ............... | A61B 17/1604 606/86 R |
| 9,297,401 B2 * | 3/2016 | Langlais | ................ | F16B 21/165 |
| 9,456,828 B2 * | 10/2016 | Kerboul | ................ | A61B 17/1659 |
| 2007/0093897 A1 * | 4/2007 | Gerbec | ................. | A61F 2/4465 623/17.11 |
| 2007/0167952 A1 * | 7/2007 | Burgi | ................... | A61B 17/162 606/99 |
| 2007/0233134 A1 * | 10/2007 | Bastian | .............. | A61B 17/1659 606/85 |
| 2008/0016636 A1 * | 1/2008 | Morris | ..................... | B25G 3/28 15/145 |
| 2012/0083769 A1 * | 4/2012 | Burgi | .................... | A61F 2/4607 606/1 |
| 2014/0263903 A1 * | 9/2014 | Ostrobrod | .......... | A62B 35/0068 248/222.12 |

* cited by examiner

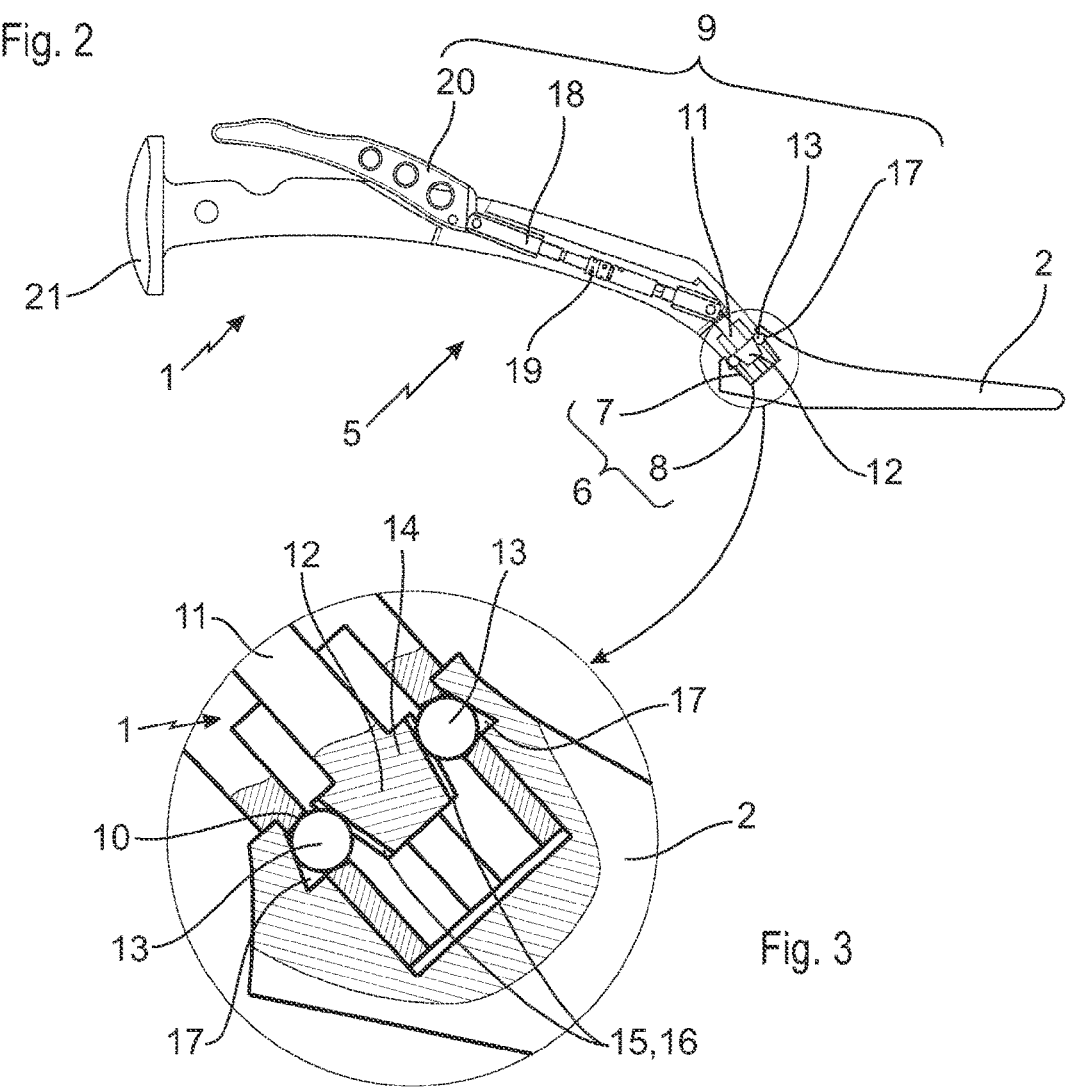

Fig. 4
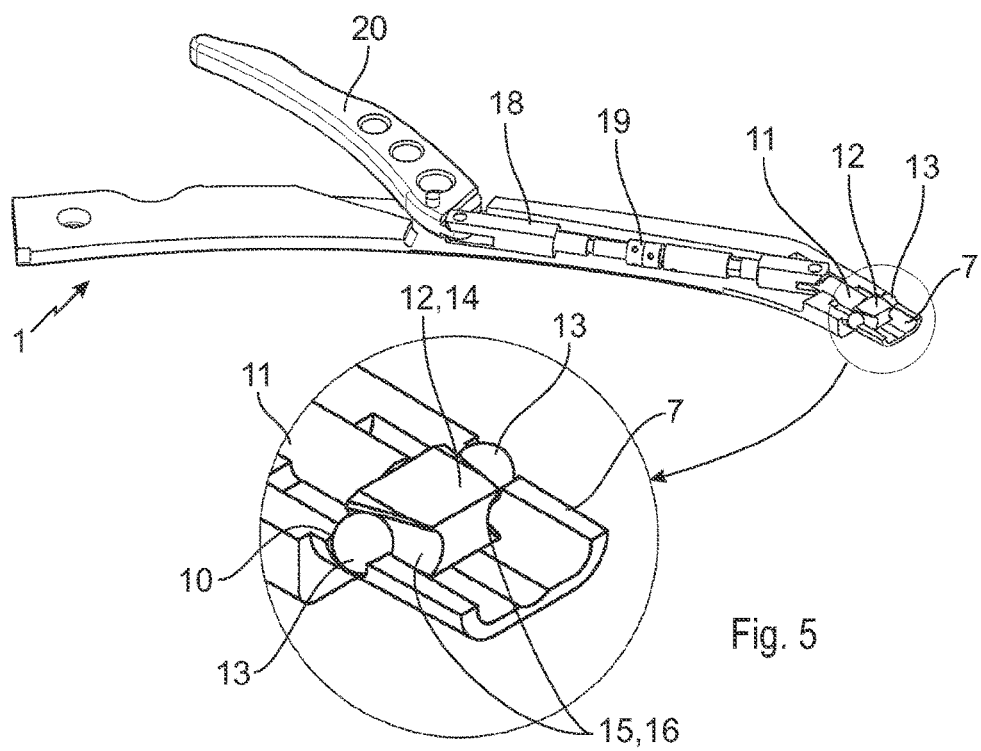
Fig. 5
Fig. 6
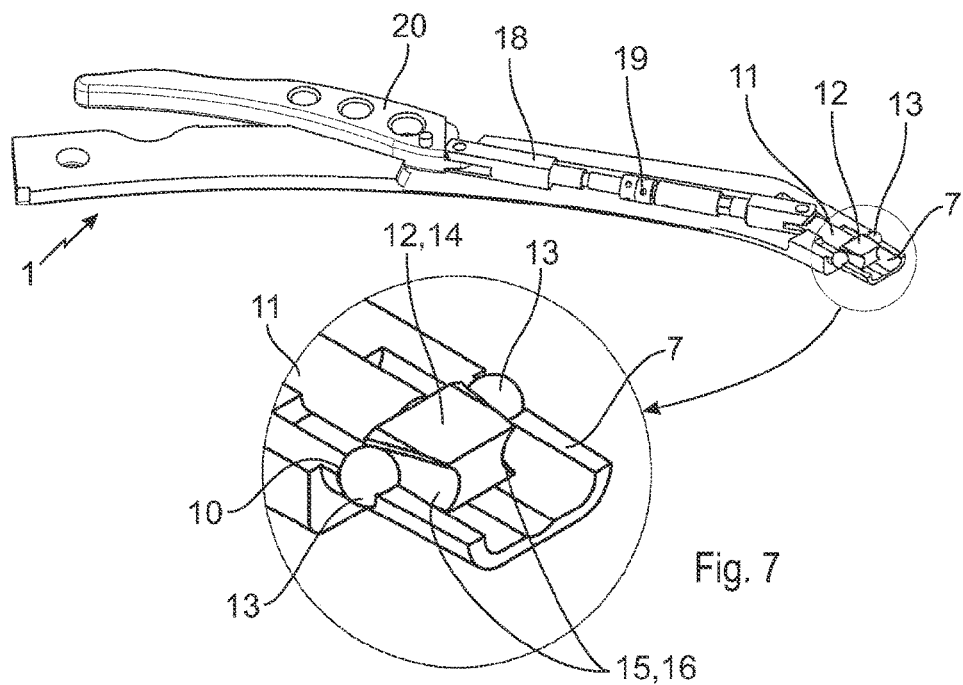
Fig. 7

REMOVABLE HANDLE PROVIDED WITH A DEVICE FOR DETACHABLE ASSEMBLY

TECHNICAL FIELD

This invention relates to a removable handle provided with a device for detachable assembly and intended to be mounted on a tool and more specifically but not exclusively on a rasp or the like used in particular for a surgeon for calibrating or grinding the end of the femur of a patient during implantation of a femoral prosthesis.

PRIOR ART

For many years already, it has been routine to provide a joint replacement, in particular the femur on the pelvis, for all or some of said joint. It is then possible to replace, with a prosthesis, the head of the femur or the acetabular cup or both of these joint elements.

For the placement more particularly of a femoral prosthesis, the surgeon must first choose, from a line of femoral prostheses, the prosthesis most adapted to the morphology of the patient and in particular the length of the femoral neck. For this choice, the surgeon must perform a certain number of tests before selecting one and placing it definitively.

Then, for the placement of the prosthesis chosen, after having removed the femoral head, the surgeon must prepare the medullary cavity of the femur using a surgical rasp or the like, the conformation of which is very similar to the rod of said prosthesis which will be engaged in the medullary canal of the femur. In order to obtain the final preparation, the surgeon will successively use a number of rasps having a homothetic shape, of increasing sizes, in order to prepare the medullary cavity in several successive steps. For this, the surgeon successively secures the different rasps to one of the ends of a removable handle in order to press each rasp into the medullary canal of the femur while tapping on the free end of said handle, the latter being provided at this free end with a hitting head and a device for quick detachable assembly of the fitting type in a direction perpendicular to the joint plane between the handle and the rasp, enabling said fitting to be locked in translation in order to prevent any undesired separation. In addition, the latest developments in hip prostheses, such as modular necks, require femoral rasps provided with a female housing capable of enabling a removable handle to be fitted.

In this regard, numerous removable handles provided with a device for detachable assembly comprising male fitting means are already known. However, the known removable handles are provided with a device for detachable assembly not making it possible to obtain blocking without play between said handles and the rasps. This residual play in particular has the effect of allowing a slight rotation and/or a slight translation of the rasp with respect to the associated handle. These slight movements may affect the assessment of the primary stability of the rasp in the femur and therefore the assessment of the primary stability of the prosthesis. This residual play may also appear over time due to wear of the parts and their assemblies.

Finally, as the housing, in particular female, of the rasps enabling the fitting of the removable handle is not entirely standardized, each prosthesis manufacturer has a line of rasps with its own housing model and therefore offers to provide the surgeon having its rasp line with a removable handle with a device for quick detachable assembly compatible with the housing of its rasps. Consequently, when the handle is broken or when the rasps are worn or broken, the surgeon must either use the same prosthesis manufacturer in order to replace the handle or the associated rasp line, or purchase prostheses from another manufacturer in order to obtain a new line of rasps as well as a new removable handle because the handles are not, in principle, compatible from one prosthesis manufacturer to another.

DESCRIPTION OF THE INVENTION

The objective of this invention is therefore to overcome the disadvantages cited above and to propose a removable handle provided with a device for detachable assembly and intended to be mounted on a tool, of the surgical rasp type or the like, said assembly device ensuring blocking without residual play enabling immobilization in translation as well as rotation of the handle with respect to the rasp, said device for detachable assembly being capable of being rendered compatible, at a low cost, with a large majority of the rasps provided with a female housing available on the market.

According to the invention, a removable handle for a tool, and more specifically, but not exclusively, for a surgical rasp or the like, is therefore proposed, the handle and the rasp cooperating at right angles to their assembly ends by contact faces which at least intersect the mean direction of transmission of forces between the handle and the rasp. Said handle comprising a device for detachable assembly is notable in that the device for detachable assembly has, on the one hand, means for assembly by fitting, in a direction generally perpendicular to said contact faces, implementing at least two complementary members, namely a hollow tenon and a mortise, respectively secured to the removable handle and the rasp and, on the other hand, means for locking said complementary members in their fitted position, i.e. when the removable handle and the rasp are secured, their contact faces being applied one against the other, said locking means comprising at least:

- a mobile slide capable of sliding at least partially inside the tenon in a direction substantially parallel to the direction of fitting of said assembly means between a "locked assembly" position in which it prevents any detachment between the removable handle and the rasp and a "free assembly" position in which it enables the handle to be released,
- a notch formed on the mortise,
- a blocking member arranged at least partially inside the tenon and capable of cooperating simultaneously with the slide and the notch when the tenon is fitted in the mortise, and
- a maneuvering lever pivoting with respect to the handle between at least two actuation positions, namely a "closed lever" position and an "open lever" position at least indirectly determining, respectively, the "locked assembly" and "free assembly" positions of the slide, and in that the respective shapes of the slide and the notch are such that, when the tenon of the handle is fitted in the mortise of the rasp and the maneuvering lever is in the "closed lever" position, the blocking member moves away toward the outside of the tenon while bearing on the notch so as to generate a clamping force, one against the other, of the respective contact faces of the handle and the rasp.

Advantageously, the locking means comprise at least one push-member articulated at each of its ends to the slide and to the maneuvering lever around axes substantially parallel to the axis of rotation of said maneuvering lever in order to transmit the movement of the maneuvering lever to the slide.

The maneuvering lever-push-member-slide assembly is configured in the form of a mechanical swivel.

The push-member is advantageously extendable. In this regard, the push-member has a screw-nut assembly with a differential pitch and/or a resilient member advantageously of the spring washer, called "Belleville" washer, type.

The tenon preferably has at least one hole passing through the thickness of said tenon, capable of receiving the blocking member and sized so as to enable the latter to go only partially beyond the outer face of the tenon while retaining it so as to prevent it from completely emerging from the hole and said tenon.

Similarly, the slide has a generally parallelepiped head, the longitudinal cross-section of which is generally trapezoidal so as to have at least one lateral face inclined with respect to the direction of fitting of the assembly means and in the direction of the free end of the tenon, said lateral inclined face comprising a longitudinal channel arranged opposite said hole when the head is inside said tenon and capable of cooperating with the blocking member.

Advantageously, the notch is arranged opposite said hole when the tenon is fitted in the mortise and inclined with respect to the direction of fitting of the assembly means and in the direction of the free end of the mortise, said notch being inclined in the opposite direction with respect to the inclination of the associated channel.

According to a preferred embodiment, the locking means comprise two blocking members and two notches formed opposite one another on the mortise along an axis substantially perpendicular to the direction of fitting of the assembly means and symmetrically with respect to the longitudinal axis of the mortise, the tenon comprises two holes arranged opposite one another along an axis substantially perpendicular to the direction of fitting of the assembly means, and the head has a longitudinal cross-section with a general regular trapezoid shape so as to have two lateral faces symmetrically inclined with respect to the direction of fitting of the assembly means and in the direction of the free end of the tenon and each comprising a longitudinal channel.

Each blocking member is advantageously a ball.

BRIEF DESCRIPTION OF THE FIGURES

Other advantages and features will become more clear from the following description of an embodiment of a removable handle provided with a device for detachable assembly according to the invention with reference to the appended figures, wherein:

FIG. 1 is a front view of a handle provided with a device for detachable assembly according to the invention associated with a rasp;

FIG. 2 is a partial view of the handle of FIG. 1 with the maneuvering lever in the "closed lever" position;

FIG. 3 is an enlarged partial vertical cross-section view of a detail of FIG. 2;

FIG. 4 is a partial perspective view of the handle similar to that of FIG. 2 with the maneuvering lever in the "open lever" position;

FIG. 5 is an enlarged detail view of the end of the handle of FIG. 4;

FIG. 6 is a partial perspective view of the handle of FIG. 2;

FIG. 7 is an enlarged detail view of the end of the handle of FIG. 6.

IMPROVED METHOD OF PRODUCING THE TECHNICAL INVENTION

A removable handle provided with a device for detachable assembly enabling the assembly of said handle on a tool, of the surgical rasp type or the like, will be described below. It goes without saying that said device for detachable assembly may be used to secure, without play, said handle on a tool of any other type without going beyond the context of this invention.

In reference to FIG. 1, the removable handle 1 is mounted on a rasp 2 used in particular by a surgeon in order to calibrate or grind the end of the femur of a patient during implantation of a femoral prosthesis. The handle 1 and the rasp 2 cooperate at right angles to their assembly ends by respective contact faces 3, 4, which at least intersect the mean direction of transmission of forces between the handle 1 and the rasp 2.

In reference to FIGS. 2 to 7, the removable handle 1 includes a device 5 for detachable assembly enabling the removable handle 1 to be mounted on the rasp 2.

The assembly device 5 includes, on the one hand, means 6 for assembly by fitting, in a direction generally perpendicular to the respective contact faces 3, 4 of the handle 1 and the rasp 2, implementing at least two complementary members, namely a tenon 7 and a mortise 8, and, on the other hand, means 9 for locking said complementary members 7, 8 in their fitted position, i.e. when the removable handle 1 and the rasp 2 are secured one with the other.

The tenon 7 and the mortise 8 advantageously have complementary generally cylindrical or conical elongate shapes, respectively secured to the removable handle 1 and the rasp 2, and extending substantially perpendicularly to their respective contact faces 3, 4.

The term cylindrical shape here refers to a shape of which the surface is defined by a straight line, called a generatrix, passing through a variable point describing a closed planar curve, called a directrix curve and maintaining a fixed direction classically perpendicular to the plane of the directrix curve.

In addition, said tenon 7 is hollow and has two holes 10 arranged opposite one another along an axis substantially perpendicular to the fitting direction of the assembly means 6 and entirely passing through the thickness of the tenon 7 so as to enable the passage from the interior to the exterior of said tenon 7.

Said locking means 9 comprise a mobile slide 11 having a generally parallelepiped head 12 capable of sliding inside the tenon 7 in a direction substantially perpendicular to the contact face 3 of the handle 1 and two blocking members 13, advantageously of the ball type, arranged inside the tenon 7. Said slide 1 is mobile between a "locked assembly" position in which the head 12 prevents any disassembly between the removable handle 1 and the rasp 2 and a "free assembly" position in which the head 12 enables the handle 1 to be released.

Said head 12 has a longitudinal cross-section with a general regular trapezoid shape so as to have two parallel lateral faces 14 and two lateral inclined faces 15 with respect to the direction of fitting of the assembly means 6 and in the direction of the free end of the tenon 7. In other words, the more one moves toward said free end, the narrower the head 12 is. The latter each comprise a longitudinal channel 16 capable of cooperating with one of the blocking members 13 and arranged opposite one of the holes 10 of the tenon 7 when the head 12 is inside said tenon 7.

Each hole 10 of the tenon 7 receives a blocking member 13 and is sized so as to enable the latter to go only partially beyond the outer face of the tenon 7 while retaining it so as to prevent it from completely emerging from the hole 10 and said tenon 7.

Said locking means 9 also comprise two notches 17 arranged on the mortise 8 of the rasp 2 arranged opposite one another along an axis substantially perpendicular to the direction of fitting of the assembly means 6, each notch 17 being arranged opposite one of the holes 10 of the tenon 7 of the handle 1 when the latter is fitted in said mortise 8. Each notch 17 has a generally rotationally cylindrical shape and is inclined with respect to the direction of fitting of the assembly means 6 and in the direction of the free end of the mortise 8. In other words, the more one moves toward said free end, the narrower the notch 17 is. Said notches 17 are symmetrical with respect to the longitudinal axis of the mortise 8 and inclined in the opposite direction with respect to the inclination of the channel 16 associated with the head 12 of the slide 11. Each notch 17 is capable of cooperating with one of the blocking members 13 in order to lock the assembly means 6.

In reference to FIGS. 2, 3, 6 and 7, when the tenon 7 of the handle 1 is fitted in the mortise 8 of the rasp 2, each blocking member 13, which is housed in a hole 10 of the tenon 7, cooperates simultaneously with a channel 16 of the head 12 of the slide 11 and a notch 17 of the mortise 8. It is thus understood that, in consideration of the inclination of the channel 16, when the maneuvering lever 20 is closed, the slide 11 moves toward the interior of the rasp 2 to the "locked assembly" position, the blocking members 13 move away toward the outside of the tenon 7, bearing on the associated notch 17. In consideration of the inclination of the notches 17, this action of the blocking members 13 has the effect of generating a clamping force one against the other of the respective contact faces 3, 4 of the handle 1 and the rasp 2. This specific technical feature makes it possible to ensure the non-detachability of the handle 1-rasp 2 assembly and in particular the suppression of any residual play between said handle 1 and rasp 2.

Conversely, in reference to FIG. 5, in order to be capable of releasing the handle 1, it is necessary for the slide 11 to move toward the inside of the handle 1 to the "free assembly" position in order to enable the blocking members 13 to be completely inserted into the tenon 7 and the assembly means 6 and therefore the handle 1 to be decoupled.

It is understood that the inclination of the channels 16 and that of the notches 17 may be inverted without going beyond the context of this invention. Thus, the head 12 will have two lateral faces 15 inclined with respect to the direction of fitting of the assembly means 6 and in the direction of the interior of the tenon 7, and each notch 17 will be inclined with respect to the direction of fitting of the assembly means 6 and in the direction of the interior of the mortise 8. With such a configuration, the slide 11 will then move toward the interior of the handle 1 so as to move from its "free assembly" position to its "locked assembly" position.

In reference to FIGS. 2, 4 and 6, the assembly device 5 includes at least one push-member 18 mobile between two so-called useful positions, including, on the one hand, a position in which it cooperates with the slide 11 precisely so as to constrict it in the "locked assembly" position and, on the other hand, another position in which it places the slide 11 in the "free assembly" position so as to enable the handle 1 and the rasp 2 to be assembled or separated.

Said push-member 18 is extensible, i.e. its length is variable so as to enable the constraint that it will exert on the slide 11 to be adjusted. Said adjustment makes it possible, on the one hand, to have the most suitable constraint value, and, on the other hand, to make up over time for the residual play in particular associated with wear of the parts constituting the assembly device 5. To do this, the push-member 18 preferably has a screw-nut assembly with a differential pitch 19 so as to enable a very small variation in the length of said push-member 18 and consequently a very precise adjustment of the constraint applied.

According to an alternative not shown, the push-member 18 has a resilient member, advantageously of the spring washer, commonly called "Belleville" washer, type.

According to another alternative not shown, the push-member 18 has a screw-nut assembly with a differential pitch 19 associated with a resilient member, the screw-nut assembly with a differential pitch 19 enabling the precise adjustment and the resilient member making it possible to smooth the handling and compensate for wear.

In reference to FIGS. 1, 2, 4 and 6, the assembly device 5 includes at least one maneuvering lever 20 pivoting with respect to the handle 1 about an axis substantially perpendicular to the longitudinal plane of symmetry of the handle 1-rasp 2 assembly of the push-member 18 between at least two actuation positions, namely a "closed lever" position in which the maneuvering lever 20 extends substantially parallel and along the handle 1 to which it is articulated (cf. FIGS. 1, 2 and 6) and an "open lever" position in which said maneuvering lever 20 forms a certain angle with said handle 1 (cf. FIG. 4). The "closed lever" and "open lever" positions at least indirectly determine the "locked assembly" and "free assembly" positions of the slide 11.

For this, the push-member 18 is articulated at each of its ends to the slide 11 and to the maneuvering lever 20 about axes substantially parallel to the axis of rotation of said maneuvering lever 20 with respect to the handle 1 so that the rotation of the latter, by an action produced in particular by closing the hand on the handle 1, drives the sliding of the slide 11 partially inside the tenon 7 in the direction of fitting of the assembly means 6 in order to block the handle 1 on the rasp 2. The push-member 18 therefore acts as a connecting rod for transmitting the movement of the maneuvering lever 20 to the slide 11.

In addition, the maneuvering lever 20-push-member 18-slide 11 assembly is configured so as to be of the mechanical swivel type, i.e. the maneuvering lever 20 is blocked when the axis of articulation between the maneuvering lever 20 and the push-member 18 has gone beyond the point of alignment between the three axes of articulation and arrives at a stop, the three axes of articulation corresponding to the two axes of articulation of the push-member 18 on the slide 11 and on the maneuvering lever 20 and the axis of rotation of said maneuvering lever 20 on the handle 1, said blocked position corresponding to the "closed lever" position of the maneuvering lever 20.

Thus, with such a configuration, when the maneuvering lever 20 is in the "closed lever" position, it remains, without the intervention of a user, in this position (cf. FIG. 2).

This special technical feature makes it possible to secure the assembly between the handle 1 and the rasp 2 while preventing any undesired opening of the maneuvering lever 20.

Among the various rasp models 2, the shapes and sizes of the mortise 8 are relatively standardized, with barely over three or four mortise models, so that by manufacturing three or four handle models 1 with a tenon 7 corresponding to the different mortise models 8, it is possible to provide, at a lower cost, a line of handles 1 compatible with all of the rasps 2 on the market. In fact, to render said handles 1 entirely compatible, it will merely be necessary to produce notches 17 on each rasp 2. Each manufacturer of prostheses and associated rasps 2 can therefore, easily and inexpensively, render its rasps compatible with the handle 1 according to the invention.

In addition, the handle 1 according to the invention may comprise only one hole 10, one blocking member 13, one channel 16 and one notch 17 without going beyond the present invention.

Finally, the handle 1 comprises a hitting area 21 (shown in FIGS. 1 and 2) at its free end so as to enable the surgeon to press each rasp into the medullary canal of the femur by tapping on said hitting area 21.

INDUSTRIAL APPLICABILITY

The handle 1 according to the invention applies more specifically to femoral rasp 2 or the like, but it may also be used for any other tool in which any residual play is to be prohibited during its assembly with said handle 1.

Finally, it goes without saying that the examples of handles 1 according to the invention described above are merely specific illustrations, which in no way limit the invention.

The invention claimed is:

1. An apparatus including a removable handle for a surgical rasp, the removable handle being configured to cooperate with the surgical rasp at respective contact faces of the removable handle and the surgical rasp, wherein the respective contact faces at least intersect a mean direction of transmission of forces between a hitting area of the removable handle and a free end of the surgical rasp, said apparatus comprising:
    a device for detachable assembly, wherein the device for detachable assembly includes:
        means for assembly in a direction of fitting generally perpendicular to said respective contact faces, the means for assembly including at least two complementary members including a hollow tenon and a mortise, respectively secured to the removable handle and the surgical rasp; and
        means for locking said at least two complementary members in a fitted position in which the removable handle and the surgical rasp are secured, the respective contact faces being applied one against the other, said means for locking including at least one of each of:
            a mobile slide capable of sliding at least partially inside the hollow tenon in a direction substantially parallel to the direction of fitting of said means for assembly between a locked assembly position in which the mobile slide prevents detachment between the removable handle and the surgical rasp and a free assembly position in which the mobile slide enables the removable handle to be released;
            a notch formed on the mortise;
            a blocking member arranged at least partially inside the hollow tenon and capable of cooperating simultaneously with the mobile slide and the notch when the hollow tenon is fitted in the mortise; and
            a maneuvering lever capable of pivoting with respect to the removable handle between at least two actuation positions including a closed lever position and an open lever position, the closed lever position and the open lever position at least indirectly determining, respectively, the locked assembly position and the free assembly position of the mobile slide,
    wherein respective shapes of the mobile slide and the notch are such that, when the hollow tenon of the removable handle is fitted in the mortise of the surgical rasp and the maneuvering lever is in the closed lever position, the blocking member moves away toward the mortise while bearing on the notch so as to generate a clamping force between the respective contact faces of the removable handle and the surgical rasp.

2. The apparatus according to claim 1, wherein the means for locking further include at least one push-member, respective ends of the at least one push-member being articulated to the mobile slide and to the maneuvering lever, respectively, around axes substantially parallel to the axis of rotation of said maneuvering lever in order to transmit movement of the maneuvering lever to the mobile slide.

3. The apparatus according to claim 2, wherein an assembly of the maneuvering lever, the at least one push-member and the mobile slide is configured in the form of a mechanical swivel.

4. The apparatus according to claim 2, wherein the at least one push-member has a variable length so as to enable constraint that will exert on the mobile slide to be adjusted.

5. The apparatus according to claim 4, wherein the at least one push-member includes a screw-nut assembly with a differential pitch.

6. The apparatus according to claim 1, wherein the hollow tenon includes at least one hole passing through the hollow tenon, capable of receiving the blocking member and sized so as to enable the blocking member to go only partially beyond an outer face of the hollow tenon while retaining the blocking member so as to prevent the blocking member from completely emerging from the at least one hole and said hollow tenon.

7. The apparatus according to claim 6, wherein the mobile slide includes a generally parallelepiped head, a longitudinal cross-section of the generally parallelepiped head being generally trapezoidal so as to have at least one lateral face inclined with respect to the direction of fitting of the means for assembly and in the direction of a free end of the hollow tenon, said at least one lateral face inclined with respect to the direction of fitting of the means for assembly including a longitudinal channel arranged opposite said at least one hole when the generally parallelepiped head is inside said hollow tenon and capable of cooperating with the blocking member.

8. The apparatus according to claim 7, wherein the notch is arranged opposite said at least one hole when the hollow tenon is fitted in the mortise and inclined with respect to the direction of fitting of the means for assembly and in the direction of a free end of the mortise, said notch being inclined in an opposite direction with respect to the inclination of the associated channel.

9. The apparatus according to claim 8, wherein the blocking member includes two blocking members and the notch includes two notches formed opposite one another on the mortise along an axis substantially perpendicular to the direction of fitting of the means for assembly and symmetrically with respect to a longitudinal axis of the mortise, said at least one hole includes two holes, said at least one lateral face inclined with respect to the direction of fitting of the means for assembly includes two lateral faces, the hollow tenon includes the two holes arranged opposite one another along an axis substantially perpendicular to the direction of fitting of the means for assembly, and the generally parallelepiped head has a longitudinal cross-section with a general regular trapezoid shape so as to have the two lateral faces symmetrically inclined with respect to the direction of fitting of the means for assembly and in the direction of the free end of the hollow tenon and each including a longitudinal channel.

10. The apparatus according to claim 1, wherein the blocking member is a ball.

11. The apparatus according to claim 3, wherein the at least one push-member has a variable length so as to enable constraint that will exert on the mobile slide to be adjusted.

12. The apparatus according to claim 2, wherein the hollow tenon includes at least one hole passing through said hollow tenon, capable of receiving the blocking member and sized so as to enable the blocking member to go only partially beyond an outer face of the hollow tenon while retaining the blocking member so as to prevent the blocking member from completely emerging from the at least one hole and said hollow tenon.

13. The apparatus according to claim 3, wherein the hollow tenon includes at least one hole passing through said hollow tenon, capable of receiving the blocking member and sized so as to enable the blocking member to go only partially beyond an outer face of the hollow tenon while retaining the blocking member so as to prevent the blocking member from completely emerging from the at least one hole and said hollow tenon.

14. The apparatus according to claim 4, wherein the hollow tenon includes at least one hole passing through said hollow tenon, capable of receiving the blocking member and sized so as to enable the blocking member to go only partially beyond an outer face of the hollow tenon while retaining the blocking member so as to prevent the blocking member from completely emerging from the at least hole and said hollow tenon.

15. The apparatus according to claim 5, wherein the hollow tenon includes at least one hole passing through said hollow tenon, capable of receiving the blocking member and sized so as to enable the blocking member to go only partially beyond an outer face of the hollow tenon while retaining the blocking member so as to prevent the blocking member from completely emerging from the at least one hole and said hollow tenon.

16. The apparatus according to claim 2, wherein the blocking member is a ball.

17. The apparatus according to claim 3, wherein the blocking member is a ball.

18. The apparatus according to claim 4, wherein the blocking member is a ball.

19. The apparatus according to claim 5, wherein the blocking member is a ball.

20. The apparatus according to claim 6, wherein the blocking member is a ball.

* * * * *